(12) United States Patent
Dhawan et al.

(10) Patent No.: US 8,188,317 B2
(45) Date of Patent: *May 29, 2012

(54) INTEGRATED PROCESS FOR THE PREPARATION OF POLYBENZIMIDAZOLE PRECURSORS

(75) Inventors: Rajiv Dhawan, Wilmington, DE (US); Joachim C. Ritter, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/634,825

(22) Filed: Dec. 10, 2009

(65) Prior Publication Data

US 2010/0160675 A1    Jun. 24, 2010

Related U.S. Application Data

(60) Provisional application No. 61/138,696, filed on Dec. 18, 2008.

(51) Int. Cl.
*C07C 211/00*    (2006.01)
(52) U.S. Cl. ........ 564/441; 564/305; 564/306; 564/415; 564/416; 562/480
(58) Field of Classification Search .................. None
See application file for complete search history.

(56) References Cited

U.S. PATENT DOCUMENTS

| | | | | |
|---|---|---|---|---|
| 3,174,947 A | * | 3/1965 | Marvel et al. | 528/331 |
| 3,476,590 A | | 11/1969 | Rabilloud, et al. | |
| 3,783,137 A | * | 1/1974 | Gerber et al. | 528/208 |
| 4,533,692 A | * | 8/1985 | Wolfe et al. | 524/417 |
| 5,041,522 A | * | 8/1991 | Dang et al. | 528/183 |
| 6,040,478 A | | 3/2000 | Sikkema et al. | |

FOREIGN PATENT DOCUMENTS

| | | |
|---|---|---|
| EP | 237955 | 7/1992 |
| JP | 2003-292476 | * 10/2003 |

OTHER PUBLICATIONS

Boyer et al, Journal of the American Chemical Society, 1960, 82, 2213-15.*
Knoblock et al. Chemische Berichte, 1958, 91, 2562-6.*
Ritter et al., U.S. Appl. No. 61/138,602, filed Dec. 18, 2008.
Ritter et al., U.S. Appl. No. 61/138,615, filed Dec. 18, 2008.
Dhawan et al., U.S. Appl. No. 61/138,626, filed Dec. 18, 2008.
Dhawan et al., U.S. Appl. No. 61/138,678, filed Dec. 18, 2008.
Ritter. U.S. Appl. No. 61/138,672, filed Dec. 18, 2008.
Dhawan et al., U.S. Appl. No. 61/138,651, filed Dec. 18, 2008.
Dhawan et al., U.S. Appl. No. 61/138,662, filed Dec. 18, 2008.
Cotton and Wilkinson, Advanced Inorganic Chemistry, Periodic Table Only, 1966, Interscience Publishers, $2^{nd}$ Edition, New York.
Blanksma, Nitro Derivatives of 2,6-Dibromotoluene, Chemisch Weekblad, 1913, vol. 9, pp. 968-973, Abstract Only.
Boyer et al., The Preparation of 6,7-Disubstituted Quinoxalines, JACS, 1960, vol. 82, pp. 2213-2215.
Knobloch et al., Synthesis of 2.6-Disubstituted Benzo (1.2.4.5) Bisimidazol, Chemische Berichte, 1958, vol. 91, pp. 2562-2565 (Machine Translated).

* cited by examiner

*Primary Examiner* — Sudhakar Katakam
(74) *Attorney, Agent, or Firm* — Kevin S. Dobson

(57) ABSTRACT

An integrated process is provided for preparing complexes of 2,3,5,6-tetraminotoluene with an aromatic diacid starting with nitration of 2,6-dihalotoluene. The process design eliminates costly intermediate drying and recrystallization steps. Handling of solid materials with possible skin sensitizing properties and toxicity is avoided, thereby eliminating human and environmental exposure.

13 Claims, 2 Drawing Sheets

INTEGRATED PROCESS FOR THE PREPARATION OF POLYBENZIMIDAZOLE PRECURSORS

This application claims priority under 35 U.S.C. §119(e) from, and claims the benefit of, U.S. Provisional Application No. 61/138,696, filed Dec. 18, 2008, which is by this reference incorporated in its entirety as a part hereof for all purposes.

TECHNICAL FIELD

This disclosure relates to methods of making complexes of 2,3,5,6-tetraminotoluene with aromatic diacids, which are then used to make high-performance polybenzimidazole polymers.

BACKGROUND

The synthesis of preferred polybenzimidazole based high performance fibers requires the selective condensation polymerization of 2,3,5,6-tetraminotoluene ("TAT") with various substituted and unsubstituted aromatic diacids, such as 2,5-dihydroxyterephthalic acid ("DHTA"). The ratio of diacid to tetraamine should be as close to 1:1 as possible to achieve high enough molecular weight to produce fibers with good enough mechanical properties. In addition, safety concerns, especially with respect to sensitizing properties of some intermediates, should be addressed.

A need thus remains for a safe, efficient process for the production of suitable high-purity TAT-diacid monomer complexes that can be polymerized to a high molecular weight polymer material for producing high-performance fibers.

SUMMARY

In one embodiment, this invention provides an integrated process for preparing a complex of 2,3,5,6-tetraminotoluene and the aromatic diacid XYTA, wherein the complex is generally described by Formula I

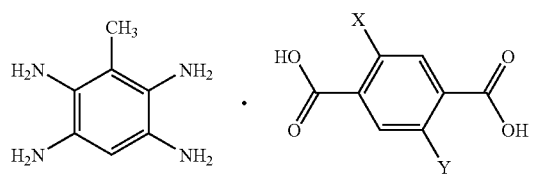

I wherein X and Y are each independently selected from the group consisting of H, OH, SH, methyl, ethyl, F, Cl, and Br; comprising the sequential steps under exclusion of oxygen:
a) nitrating 2,6-dihalotoluene (II)

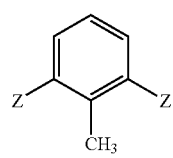

II wherein each Z is independently Cl or Br, in a reaction mixture comprising oleum or $SO_3$, nitric acid, and $H_2SO_4$ wherein
  (i) the concentration of nitric acid is about 2.0 to about 2.3 moles per mole of 2,6-dihalotoluene;
  (ii) the concentration of $SO_3$ is about 1 to about 3 moles per mole of 2,6-dihalotoluene and
  (iii) the concentration of 2,6-dihalotoluene in the reaction mixture is between about 12 and about 24 weight percent; and
wherein the temperature of the reaction mixture does not exceed 120° C.; thereby producing 2,6-dihalo-3,5-dinitrotoluene;
b) directly separating the 2,6-dihalo-3,5-dinitrotoluene from the reaction mixture by filtration, while recycling the sulfuric acid mother liquor;
c) washing the 2,6-dihalo-3,5-dinitrotoluene with water or acid then water, then with $NH_4OH$, and then mixing it with glycol as a suspension;
d) aminating the 2,6-dihalo-3,5-dinitrotoluene by heating the suspension formed in step (c) to a temperature in the range of about 100° C. to about 160° C. and contacting it with $NH_3(g)$, thereby converting the 2,6-dihalo-3,5-dinitrotoluene to 2,6-diamino-3,5-dinitrotoluene;
e) directly separating the 2,6-diamino-3,5-dinitrotoluene from the reaction mixture by filtration, washing with glycol, then washing with water;
f) forming a slurry of the 2,6-diamino-3,5-dinitrotoluene with water and transferring the slurry to a hydrogenation reactor containing a hydrogenation catalyst to form a reaction mixture;
g) hydrogenating the 2,6-diamino-3,5-dinitrotoluene by contacting the reaction mixture formed in step (f) with hydrogen at a pressure in the range of about 0.31 to about 3.45 MPa and a temperature in the range of about 20° C. to about 100° C. to hydrogenate the 2,6-diamino-3,5-dinitrotoluene, thereby producing 2,3,5,6-tetraminotoluene;
h) contacting the 2,3,5,6-tetraminotoluene produced in (a) with an aqueous solution comprising 1 to 6 equivalents of acid per mol of 2,3,5,6-tetraminotoluene, optionally heating the solution, thereby dissolving the 2,3,5,6-tetraminotoluene;
i) filtering the reaction mixture, thereby removing the spent hydrogenation catalyst;
j) combining the filtered reaction mixture with
  i) 0 to 5 equivalents of an acid selected from the group consisting of HCl, acetic acid, $H_2SO_4$, and $H_3PO_4$;
  ii) 0 to 5 equivalents of an organic base or an inorganic base;
  iii) optionally, a buffer solution; and
  iv) an XYTA source selected from XYTA and $M_2XYTA$ (Formula III)

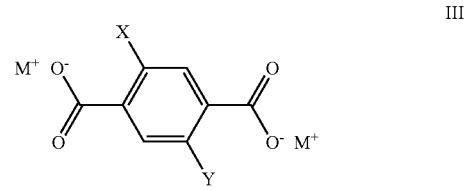

III wherein M is K or Na, and wherein the molar ratio of XYTA to the 2,3,5,6-tetraminotoluene salt is from 1:1 to 1:1.1; thereby adjusting the pH of the mixture to between about 3 and about 10 and thereby producing and precipitating the complex generally described by Formula (I); and k) cooling, filtering, and washing the precipitated complex.

In another embodiment, this invention provides an integrated process for preparing a complex of 2,3,5,6-tetraminotoluene and the aromatic diacid XYTA, wherein the complex is generally described by Formula I

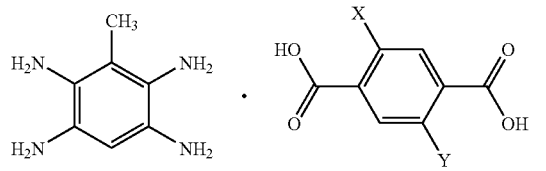

wherein X and Y are each independently selected from the group consisting of H, OH, SH, methyl, ethyl, F, Cl, and Br; comprising the sequential steps under exclusion of oxygen:

a) nitrating 2,6-dihalotoluene (II)

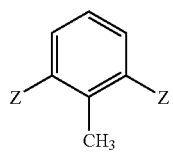

wherein each Z is independently Cl or Br, in a reaction mixture comprising oleum or $SO_3$, nitric acid, and $H_2SO_4$ wherein
(i) the concentration of nitric acid is about 2.0 to about 2.3 moles per mole of 2,6-dihalotoluene;
(ii) the concentration of $SO_3$ is about 1 to about 3 moles per mole of 2,6-dihalotoluene; and
(iii) the concentration of 2,6-dihalotoluene in the reaction mixture is between about 12 and about 24 weight percent; and wherein the temperature of the reaction mixture does not exceed 120° C.; thereby producing 2,6-dihalo-3,5-dinitrotoluene;

b) directly separating the 2,6-dihalo-3,5-dinitrotoluene from the reaction mixture by filtration, while recycling the sulfuric acid mother liquor;

c) washing the 2,6-dihalo-3,5-dinitrotoluene with water or acid then water, then with $NH_4OH$, and then mixing it with glycol as a suspension;

d) aminating the 2,6-dihalo-3,5-dinitrotoluene by heating the suspension formed in step (c) to a temperature in the range of about 100° C. to about 160° C. and contacting it with $NH_3(g)$, thereby converting the 2,6-dihalo-3,5-dinitrotoluene to 2,6-diamino-3,5-dinitrotoluene;

e) directly separating the 2,6-diamino-3,5-dinitrotoluene from the reaction mixture by filtration, washing with glycol, then washing with water;

f) forming a slurry of the 2,6-diamino-3,5-dinitrotoluene with water and transferring the slurry to a hydrogenation reactor containing a hydrogenation catalyst to form a reaction mixture;

g) hydrogenating the 2,6-diamino-3,5-dinitrotoluene by contacting the reaction mixture formed in step (f) with hydrogen at a pressure in the range of about 0.31 to about 3.45 MPa and a temperature in the range of about 20° C. to about 100° C. to hydrogenate the 2,6-diamino-3,5-dinitrotoluene, thereby producing 2,3,5,6-tetraminotoluene;

h) contacting the 2,3,5,6-tetraminotoluene produced in (g) with an aqueous solution comprising 1 to 6 equivalents of acid per mol of 2,3,5,6-tetraminotoluene, optionally heating the solution, thereby dissolving the 2,3,5,6-tetraminotoluene;

i) filtering the reaction mixture, thereby removing the spent hydrogenation catalyst;

j) forming and precipitating the 2,3,5,6-tetraminotoluene salt by adding an acid to the filtered reaction mixture, wherein the acid is selected from the group consisting of HCl, acetic acid, $H_2SO_4$, and $H_3PO_4$;

k) cooling, filtering, washing and dissolving the precipitated 2,3,5,6-tetraminotoluene salt to form an aqueous solution thereof;

l) combining the 2,3,5,6-tetraminotoluene salt solution with
(i) 0 to 5 equivalents of an acid selected from the group consisting of HCl, acetic acid, $H_2SO_4$, and $H_3PO_4$;
(ii) 0 to 5 equivalents of an organic base or an inorganic base;
(iii) optionally, a buffer solution; and
(iv) 0 to 5 equivalents of an XYTA source selected from XYTA and $M_2$XYTA (Formula III)
wherein M is K or Na, and wherein the molar ratio of XYTA to the 2,3,5,6-tetraminotoluene salt is from 1:1 to 1:1.1; thereby adjusting the pH of the mixture to between about 3 and about 10 and thereby producing and precipitating the complex generally described by Formula (I); and m) cooling, filtering, and washing the precipitated complex.

BRIEF DESCRIPTION OF THE DRAWINGS

The invention is illustrated by way of example and not limitation in the accompanying figures.

DETAILED DESCRIPTION

Figure 1:
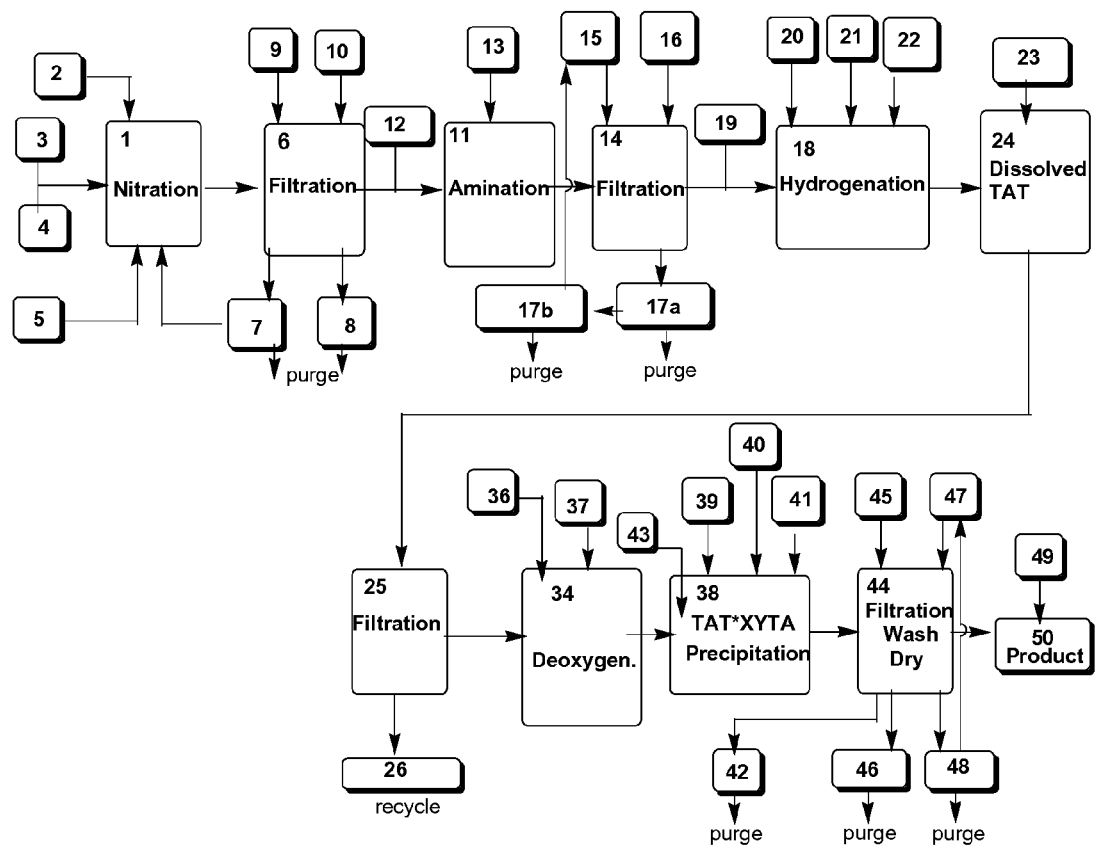
FIG. 1 is a schematic representation of one embodiment of the process described herein.

The following description is exemplary and explanatory only and is not restrictive of the invention, as defined in the appended claims.

An integrated process is provided for preparing a complex of 2,3,5,6-tetraminotoluene and the aromatic diacid XYTA, wherein the complex is generally described by Formula I

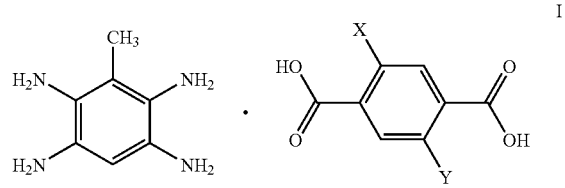

wherein X and Y are each independently selected from the group consisting of H, OH, SH, methyl, ethyl, F, Cl, and Br; comprising the sequential steps under exclusion of oxygen of:

a. nitration of 2,6-dihalotoluene (II)

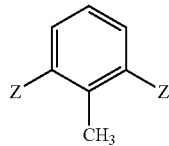

wherein each Z is independently Cl or Br, in a reaction mixture comprising oleum or $SO_3$, nitric acid, and $H_2SO_4$
wherein
  (i) the concentration of nitric acid is about 2.0 to about 2.3 moles per mole of 2,6-dihalotoluene;
  (ii) the concentration of $SO_3$ is about 1 to about 3 moles per mole of 2,6-dihalotoluene;
  (iii) the concentration of 2,6-dihalotoluene in the reaction mixture is between about 12 and about 24 weight percent; and
wherein the temperature of the reaction mixture does not exceed 120° C.; thereby producing 2,6-dihalo-3,5-dinitrotoluene;

b. directly separating the 2,6-dihalo-3,5-dinitrotoluene from the reaction mixture by filtration, while recycling the sulfuric acid mother liquor;

c. washing the 2,6-dihalo-3,5-dinitrotoluene with water or acid then water, then with $NH_4OH$, and then mixing it with glycol as a suspension;

d. aminating the 2,6-dihalo-3,5-dinitrotoluene by heating the suspension formed in step (c) to a temperature in the range of about 100° C. to about 160° C. and contacting it with $NH_{3(g)}$, thereby converting the 2,6-dihalo-3,5-dinitrotoluene to 2,6-diamino-3,5-dinitrotoluene;

e. directly separating the 2,6-diamino-3,5-dinitrotoluene from the reaction mixture by filtration, washing with glycol, then washing with water;

f. forming a slurry of the 2,6-diamino-3,5-dinitrotoluene with water and transferring the slurry to a hydrogenation reactor containing a hydrogenation catalyst to form a reaction mixture;

g. hydrogenating the 2,6-diamino-3,5-dinitrotoluene by contacting the reaction mixture formed in step (f) with hydrogen at a pressure in the range of about 0.31 to about 3.45 MPa and a temperature in the range of about 20° C. to about 100° C. for sufficient time to hydrogenate the 2,6-diamino-3,5-dinitrotoluene, thereby producing 2,3,5,6-tetraminotoluene;

h. contacting the 2,3,5,6-tetraminotoluene produced in (g) with an aqueous solution comprising 1 to 6 equivalents of acid per mol of 2,3,5,6-tetraminotoluene, optionally heating the solution, thereby dissolving the 2,3,5,6-tetraminotoluene;

i. filtering the reaction mixture, thereby removing the spent hydrogenation catalyst;

j. combining the filtered reaction mixture with
  i. 0 to 5 equivalents of an acid;
  ii. 0 to 5 equivalents of an organic base or an inorganic base;
  iii. optionally, a buffer solution; and
  iv. an XYTA source selected from XYTA and $M_2XYTA$ (Formula III)

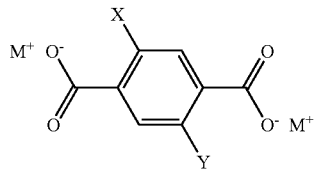

wherein M is K or Na, and wherein the molar ratio of XYTA to the 2,3,5,6-tetraminotoluene salt is from 1:1 to 1:1.1; thereby adjusting the pH of the mixture to between about 3 and about 10 and thereby producing and precipitating the complex generally described by Formula (I); and k. cooling, filtering, and washing the precipitated complex.

Further provided is a process in which a TAT salt is produced in a separate step by adding acid to the filtered reaction mixture produced in step (i) followed by cooling and filtration, dissolution of the TAT salt, formation and precipitation of the TAT.XYTA complex via addition of XYTA or XYTA salt, addition of aqueous base, and cooling. This embodiment produces higher purity TAT.XYTA complex without the need to use carbon bed filters and allows for more flexibility in terms of production (timing) and easier dosage.

In the context of this disclosure, a number of terms shall be utilized.

As used herein, the term "TAT salt" or, equivalently, "2,3,5,6-tetraminotoluene salt," denotes a compound formed by reaction of 2,3,5,6-tetraminotoluene salt with an acid such as HCl, acetic acid, $H_2SO_4$, or $H_3PO_4$. One example of a TAT salt is TAT.4HCl.

As used herein, the term "XYTA" denotes 2-X-5-Y-terephthalic acid, where X and Y each independently selected from the group consisting of H, OH, SH, methyl, ethyl, F, Cl, and Br. One example is 2,5-dihydroxyterephthalic acid, in which X=Y=OH. The disodium or dipotassium salt of the diacid is represented by the term "$M_2XYTA$" where M is Na or K.

As used herein, the term "oleum" denotes fuming sulfuric acid, which is anhydrous and is formed by dissolving excess sulfur trioxide ($SO_3$) into sulfuric acid.

As used herein, the term "fuming nitric acid" denotes concentrated nitric acid containing dissolved nitrogen dioxide.

As used herein, the term "net yield" of P denotes the actual, in-hand yield, i.e., the theoretical maximum yield minus losses incurred in the course of activities such as isolating, handling, drying, and the like.

As used herein, the term "purity" denotes what percentage of an in-hand, isolated sample is actually the specified substance.

The process is designed in such a way that solids handling is avoided. Filtered materials are transferred, without prior drying, in the form of suspension slurries in the solvent that is used for the respective reaction step. This process design thereby avoids costly drying processes. It also avoids the handling of solid materials with possible skin sensitizing properties and toxicity, and eliminates human and environmental exposure to them.

One embodiment of the process described here is illustrated in FIG. 1; possible minor modifications will be evident to one skilled in the art. With reference to the embodiment shown in FIG. 1, the process starts with the nitration 1 of 2,6-dihalotoluene, "mDHT" (i.e., 2,6-dichlorotoluene or 2,6-dibromotoluene; 2,6-dichlorotoluene is preferred), in a reaction mixture prepared by combining the 2,6-dihalotoluene 2; sulfuric acid; oleum 3 or $SO_3$ 5; and nitric acid 4. The concentration of nitric acid is about 2.0 to about 2.3 moles per mole of 2,6-dihalotoluene. Concentrated nitric acid (e.g., commonly used reagent grade, which is about 70% nitric acid in water) can be used, but fuming nitric acid is preferred.

If concentrated nitric acid is used, since in the process described herein water must be kept at a level below one equivalent to get highly pure product, more $SO_3$ would be added to remove the water from the nitric acid (by reacting with it to form sulfuric acid) and still have sufficient $SO_3$ present in the reaction mixture for the nitration reaction. The concentration of $SO_3$ is about 1 to about 3 moles, preferably 1.5 to 2 moles, per mole of 2,6-dihalotoluene. The sulfuric acid is present in an amount such that the weight percent of mDHT in the reaction mixture (i.e., the weight of mDHT relative to the combined weight of mDHT plus the acid solution) is between 12 and 24 weight percent.

The nitration reaction is carried out at a temperature not to exceed about 120° C., typically in the range of about 5° C. to about 100° C., preferably in the range of about 5° C. to about 40° C., and more preferably in the range of about 5° to about 15° C. The 2,6-dihalo-3,5-dinitrotoluene thereby produced is separated directly by filtration 6 from the reaction mixture as a crude crystal cake without quench or recrystallization steps. The crude crystal cake is washed (9, 10) with water or with acid (e.g., concentrated or dilute sulfuric acid) then water; and is then washed with $NH_4OH$. Aqueous waste is discarded 8. The sulfuric acid mother liquor is recycled 7, 1 with a purge drawn to prevent excess sulfuric acid accumulation. The resulting wet cake of 2,6-dihalo-3,5-dinitrotoluene is then mixed with glycol 12 and introduced into the amination reactor 11 as a suspension.

The suspension is heated to a temperature in the range of about 100° C. to about 160° C., preferably about 140° C., to dissolve the 2,6-dihalo-3,5-dinitrotoluene in the glycol. The resulting solution is contacted at that temperature with gaseous $NH_3$ 13 for approximately four to eight hours close to ambient pressure; the $NH_3$ is fed as it is consumed. At reaction completion, the 2,6-diamino-3,5-dinitrotoluene thereby produced is filtered 14, typically at about 60° C., and washed with glycol 15 and then water 16. The mother liquor (filtrate) containing glycol is collected 17a, and the glycol is distilled and recycled 17b, 15; purges are drawn to prevent accumulation. The wet cake of 2,6-diamino-3,5-dinitrotoluene is slurried with water 19 and transferred to the hydrogenation reactor 18 as a suspension.

The hydrogenation reactor also contains a hydrogenation catalyst 22. Suitable hydrogenation catalysts comprise metal and/or metal salt; examples include without limitation Pd/C and Pt/C and mixtures thereof, optionally containing other metals from Groups VIII through X such as Fe. The groups are as described in the Periodic Table in *Advanced Inorganic Chemistry* by F. A. Cotton and G. Wilkinson, Interscience New York, 2nd Ed. (1966). Of these, Pt/C is preferred. The catalyst is typically used in the amount of about 0.5 to about 5.0 wt % metal based on 2,6-diamino-3,5-dinitrotoluene.

The hydrogenation reactor is purged with nitrogen, and the aqueous suspension is contacted with hydrogen 21 in the presence of about 0 to about 1 mol equivalent of $NH_{3(g)}$ 20 to form a reaction mixture. The reaction is carried out at a temperature in the range of about to 20° C. to 100° C., preferably about 60° C. to about 85° C., and a hydrogen pressure of about 45 to about 500 psi (0.31 to 3.45 MPa) preferably about 300 psi (2.07 MPa). Reaction continues for a time sufficient to consume about 6 to 7 mol equivalents of hydrogen, thereby producing 2,3,5,6-tetraminotoluene ("TAT"). The time required depends on the details of the specific set up but is typically about 2 hours.

As shown in FIG. 1, about 1 to about 6 equivalents, preferably about 1 to about 3 equivalents, of an acid 23 are added to dissolve the TAT; as a result, a soluble acid salt of TAT is formed, herein referred to as "TAT salt." Any acid which allows for the dissolution of TAT in water and its subsequent re-precipitation is suitable. The selection of the acid depends on the specific needs and is based on solubility data and is easily done by one skilled in the art. Examples of suitable acids include without limitation HCl, acetic acid, $H_2SO_4$, and $H_3PO_4$. HCl is preferred, and the TAT salt generally prepared is TAT.4HCl. The solution may be heated to facilitate dissolution. Optionally, a co-solvent may be present. Examples of co-solvents include without limitation methanol, ethanol, and isopropanol. Optionally, the solution may be filtered through an absorbent material capable of absorbing impurities. Examples of absorbent materials include without limitation active carbon, alumina and microporous styrene.

The resulting reaction mixture 24 is then filtered 25, typically at a temperature in the range of about 60° C. to about 80° C. to remove the spent hydrogenation catalyst 26, preferably by passing through a carbon filter bed. The spent catalyst can then be recycled.

Because the filtered reaction mixture may have picked up small amounts of oxygen, nitrogen 36 is typically blown through it 34 in a deoxygenation step. A small amount of tin 37 (e.g., about 0.5 wt % tin powder) may be added as well to reduce oxidized species and prevent additional oxidation. The temperature at this stage is typically about 35° C. to about 40° C.

The complex TAT.XYTA (Formula I) is produced by combining the filtered, deoxygenated reaction mixture with about 1 to about 5 equivalents of a source of the XYTA moiety 39 and adjusting the pH to precipitate the complex. This is done under a nitrogen atmosphere 43 to exclude oxygen. The XYTA source can be the diacid XYTA, the salt $M_2XYTA$ (M=K or Na), or a mixture of diacid XYTA and salt $M_2XYTA$. The pH is adjusted to between about 3 and about 10, preferably between about 5 and about 8, i.e., the pH range at which the complex is least soluble, to precipitate the desired 1:1 complex and maximize yield. The pH is adjusted to the desired value using 0 to 5 equivalents of an acid; 0 to 5 equivalents of an organic base or an inorganic base; and, optionally, a buffer solution. Water may be used as well.

Examples of suitable acids include without limitation HCl, acetic acid, $H_2SO_4$, and $H_3PO_4$. Examples of suitable organic bases include without limitation aliphatic amines (for example, triethylamine) and carboxylates like acetate (acetate might need to be used in conjunction with a stronger base). Examples of suitable inorganic bases include without limitation KOH, NaOH, alkali carbonates, alkali bicarbonates, and ammonia. The acids and/or bases should not form undesirable products irreversibly when added to the reaction mixture. Also, any salt byproducts produced during complex formation should be readily removable (e.g., soluble in the reaction mixture or extractable with a solvent that does not dissolve the complex).

In the embodiment shown in FIG. 1, streams of water 40 and a basic solution 41 (for example, 2 equivalents NaOH) are added. The temperature of the mixture is initially about 40° C. to about 100° C., typically about 50° C. to about 60° C., and is gradually cooled to promote complete precipitation of the complex. The preferred precipitation temperature will depend on the product concentration and on the amount of impurities present, but is generally chosen between about 0° and about 40° C., preferably between about 0° and about 20° C.

Various designs are possible for combining the TAT salt solution with the XYTA source and whatever acid, base, and/or buffer solutions are used to adjust the pH. FIG. 1 shows one embodiment in which a stream of TAT salt in an acid solution 34, the XYTA source 39, water 40, and base 41 are fed concurrently or consecutively into a vessel 38 wherein complex formation and precipitation take place. The XYTA source 39, water 40, and base 41 are most conveniently added as a single solution. In other embodiments, TAT salt in an acid solution could be introduced into a vessel containing a basic XYTA source solution, or the XYTA source stream could be fed into the vessel containing the TAT salt in an acid solution. Alternatively, the XYTA source and TAT salt could be fed concurrently or consecutively into a buffer solution at the desired pH or into a basic solution to which an acid solution is subsequently added.

The TAT.XYTA complex is recovered from the reaction mixture by filtration at a temperature in of the range of about 5° C. to about 50° C., preferably about 10° C. to about 15° C., and washed with water 45 and methanol 47, typically at a temperature in the range of about 15° C. to about 40° C. The methanol is recycled (47, 48) and a purge is drawn to prevent accumulation. Aqueous wastes are discarded. In the embodiment shown in FIG. 1, there are two purge streams for aqueous wastes (42, 46), one of which (42) contains most of the Sn used in the deoxygenation step. The washed and dried TAT.XYTA complex 50 is kept under nitrogen 49 to protect it from oxygen. It is of high enough quality and purity to produce polybenzimidazole polymer of high enough molecular weight to make high performance fibers.

Figure 2:
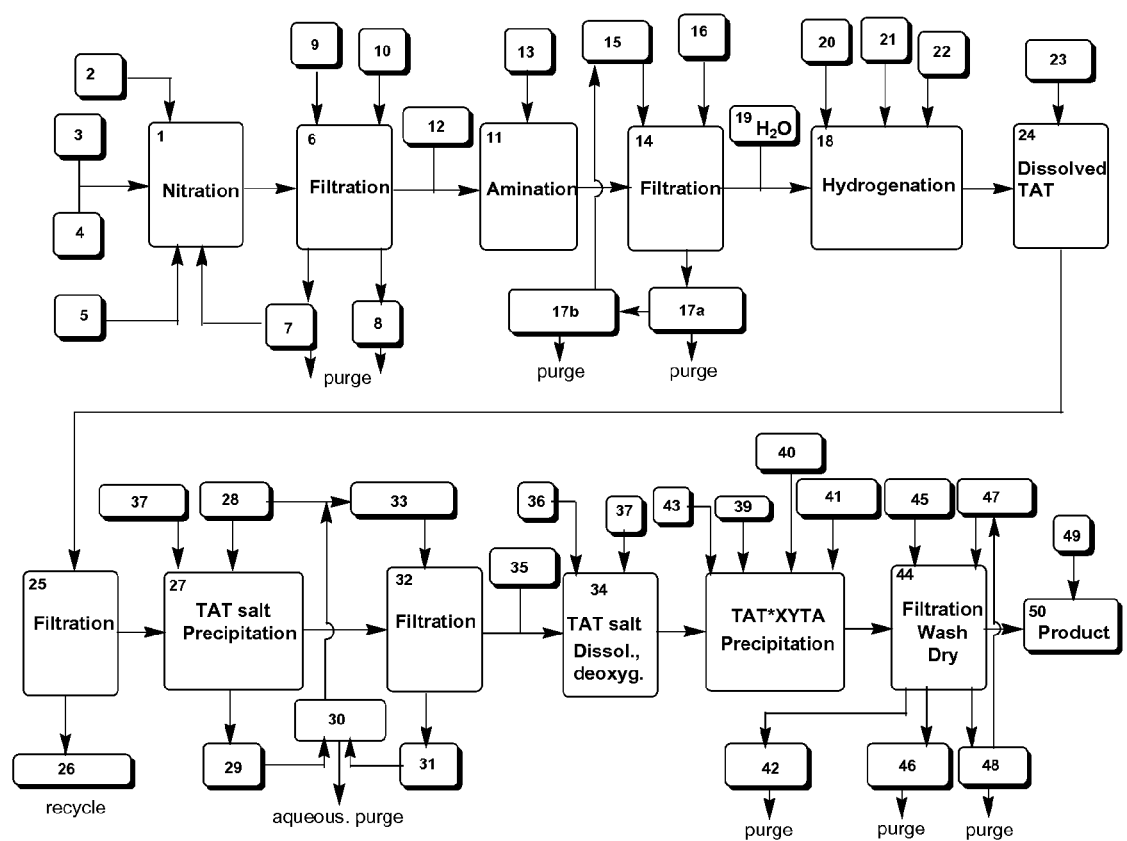
FIG. 2 is a schematic representation of another embodiment of the process described herein, in which 2,3,5,6-tetraminotoluene salt is precipitated and washed then used to make the complex.

In another embodiment of the process described herein, illustrated in FIG. 2, acid is added 28 at a temperature in the range of about 10° C. to about 80° C. to form and precipitate the TAT salt 27, for example, TAT.4HCl. Examples of suitable acids include without limitation HCl, acetic acid, $H_2SO_4$, and $H_3PO_4$. HCl is preferred. The amount of acid needed for this step will depend on the concentration of TAT in the filtrate and is readily determined by one skilled in the art. Typically, about 6 to about 8 equivalents of acid (as for example, 38% $HCl_{aq}$) are needed in this step to precipitate the TAT salt (for example, as TAT.4HCl) in about 90% yield. The use of gaseous acid, such as gaseous HCl, might reduce the total volume of liquid needed since the additional introduction of water with aqueous acid in both addition steps increases the absolute solubility of the TAT salt in the filtered reaction mixture. The addition of equivalent amounts of acid in the gas phase instead of as an aqueous solution (for example, $HCl_{gas}$ instead of $HCl_{aq}$) is preferred since the liquid volumes are thereby reduced, and crystallization yields are expected to be higher as a consequence. Aqueous acid (for example, 30-38 wt % HCl) may be used because it is easier to handle than the acid in the gas phase. Aqueous acid can be recovered 29, distilled 30, and recycled (30, 28) or used in the acid wash step of the process (30, 33, 44).

A small amount of tin (e.g., about 0.5% tin powder) is optionally added 37 to reduce impurities caused by oxidation and to prevent further impurity formation by that route.

The reaction mixture containing the precipitated TAT salt is then cooled to about 5° C. to about 15° C. and stirred, then filtered 32. The TAT salt is then washed with deaerated aqueous acid, such as concentrated HCl 33. The used aqueous acid can then be distilled and recycled (31, 30, 33). Water is added 35 to dissolve the washed TAT salt 34. Although filtration 32 and salt dissolution 34 are shown as occurring in separate vessels in the embodiment illustrated in FIG. 2, a single vessel could be used. After the TAT salt is dissolved 34, the TAT.XYTA formation and precipitation, filtration, washing, and drying are carried out as described above (36 through 50).

The embodiment illustrated in FIG. 2 can produce higher purity TAT.XYTA complex without the need to use carbon bed filters and allows for more flexibility in terms of production (timing) and easier dosage. The embodiment illustrated in FIG. 1, on the other hand, reduces the amount of waste salt and also the amount of acid (e.g., HCl) and base (e.g., NaOH) needed, thus lessening raw material cost. Both embodiments produce polymer grade material suitable for the manufacture of high-performance fibers.

The process described herein is an efficient and effective way to produce high purity TAT.XYTA complexes, particularly the 1:1 complex of TAT and 2,5-dihydroxyterephthalic acid, which can be used to make polybenzimidazole polymer for high performance fibers. This process design eliminates costly intermediate drying and recrystallization steps. The recycling of spent catalyst and of sulfuric acid, glycol, and methanol streams contributes economical and environmental advantages. And, importantly, handling of solid materials with possible skin sensitizing properties and toxicity is avoided, thereby eliminating human and environmental exposure.

The materials, methods, and examples herein are illustrative only and, except as specifically stated, are not intended to be limiting.

EXAMPLES

The present invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

The meaning of abbreviations is as follows: "d" means density, "DADNT" means 1,3-diamino-4,6-dinitrotoluene, "g" means gram(s), "GC" means gas chromatography, "$^1$H-NMR" means proton nuclear magnetic resonance spectroscopy, "h" means hour(s), "L" means liter(s), "mg" means milligram(s), "mL" means milliliter(s), "min" means minutes, "mol" means mole(s), "mmol" means millimole(s), "MPa" means megapascals, "psi" means pounds per square inch, and "UV" means ultraviolet spectroscopy.

Example 1

This Example demonstrates the preparation of 2,6-dichloro-3,5-dinitrotoluene.

To a 1 L 4-neck round bottom flask equipped with external ice cooling, mechanical stirrer, addition funnel, $N_2$ inlet, and thermometer was added 118 g (1.872 mmol) fuming nitric acid (d=1.54). With cooling, 745 g (1863 mmol $SO_3$) 20% oleum was added over a period of 30 minutes while maintaining a temperature below 30° C. The acid solution was cooled to 0-5° C. and 150 g (932 mmol) 2,6-dichlorotoluene was slowly added over 2 h while maintaining a temperature below 20° C. When addition was complete, the ice bath was removed and the reaction mixture was slowly allowed to warm to room temperature. It was then heated from room temperature to 110° C. over a time period of 45 min. After 15 min at 110° C., the reaction mixture was allowed to cool to room temperature and then cooled to 5° C. It was then filtered through a glass fritted funnel and washed with 250 mL water followed by 250 mL 10% aqueous $NH_3$ solution to yield a pale yellow crystalline wet cake. A small sample was dried in vacuum and analyzed by both $H^1$-NMR and GC and found to be 99.9% pure. The wet cake (219 g) contained about 201.5 g 2,6-dichloro-3,5-dinitrotoluene and 17.5 g water. The net yield of 2,6-dichloro-3,5-dinitrotoluene amounted to about 86%.

Example 2

This example demonstrates the preparation of 2,6-diamino-3,5-dinitrotoluene from 2,6-dichloro-3,5-dinitrotoluene.

A 3 L round bottom flask equipped with stirring, temperature control, gas inlet tube, and reflux condenser was charged with 200 g of the wet cake 2,6-dichloro-3,5-dinitrotoluene (733 mmol) that was prepared in Example 1 and 1 L oxygen-free ethylene glycol and was heated to a reaction temperature of 140° C. When the reaction temperature was reached, anhydrous $NH_3$ was slowly added at the rate at which it was consumed. The reaction was monitored by GC. When ammonia uptake was completed the heat was removed and the reaction mixture was allowed to cool to 60° C. The crystalline product was collected via suction filtration. The orangish-brown crystalline solid was washed with 200 mL ethylene glycol and 200 mL water.

A total of 164 g of wet cake product was isolated. A portion of the wet cake material was analyzed by $^1$H-NMR and found to have a purity of 88% with 7% 2-amino-6-chloro-3,5-dinitrotoluene and 2% ethylene glycol and 3% water remaining, corresponding to 93% net yield of 2,6-diamino-3,5-dinitrotoluene product. About 119 g of the crude wet cake material were carried on to the next step (Example 3).

Example 3

This example demonstrates the preparation of TAT.4HCl from 2,6-diamino-3,5-dinitrotoluene.

A 1 L stirred Hastelloy autoclave was charged with 119 g of crude DADNT wet cake (about 0.49 mol), and 2.4 g of 5% Pt/C catalyst. The autoclave was purged 5 times with $N_2$ and 2 times with $H_2$ at 90 psi (0.62 MPa). Subsequently, 600 mL of deaerated water (purged with $N_2$ overnight) was added and the mixture was pressurized at 81° C. to 300 psi (2.07 MPa). Hydrogenation was continued for a total time of 3 h with an approximate uptake of 6.5 mol equivalents of $H_2$. The excess hydrogen was released and the autoclave was cooled to 40° C. and purged twice with $N_2$, after which 240 g of deaerated $HCl_{aq}$ (34%, by titration) was added. The mixture was stirred and heated back up to 80° C., then passed through a carbon bed filter at 75° C. to remove catalyst and a small amount of unconverted starting material. A total of about 1.0 L of a red-orange colored reaction solution was collected containing an equivalent of approximately 134 g of TAT.4HCl. (0.45 mol). A portion of this solution was directly used in Example 4.

Example 4

This example demonstrates the preparation of TAT.DHTA from crude TAT.4HCl solution.

12.47 g of $K_2$DHTA (45.52 mmol) along with 5.82 g of sodium hydroxide (145.45 mmol) was added to a reaction vessel. This was followed by the addition of 180 mL of deaerated water and heating to 75° C. About 100 g of the aqueous TAT.4HCl salt solution made in Example 4 (equivalent to about 12.4 g of 2,5-diamino-3,5-dinitrotoluene) was combined with 100 mg of tin powder (0.91 mmol) and heated to 75° C. to effect complete dissolution. The TAT salt solution was subsequently pumped into the basic $K_2$DHTA solution over a period of 5 minutes, which resulted in precipitation of a yellow solid. This mixture was then cooled to 25° C. with stirring for 1.5 hours. The mixture was subsequently filtered and washed with water (50 mL) and methanol (50 mL). The solid light yellow product was allowed to dry for 18 hours under a stream of nitrogen at 40° C.

The net yield of TAT.DHTA product was 12.8 g (80%). $^1$H-NMR analysis indicated product purity>99% with a TAT:DHTA ratio of 1.00:1.01. The material was analyzed by UV for oxidative decomposition products 3,6-diimino-2-methyl-cyclohexa-1,4-diene-1,4-diamine (Formula IV), 1,9-dimethylphenazine-2,3,7,8-tetraamine (Formula V), and 1,6-dimethylphenazine-2,3,7,8-tetraamine (Formula VI). No V or VI and less than 100 ppm of IV were detected.

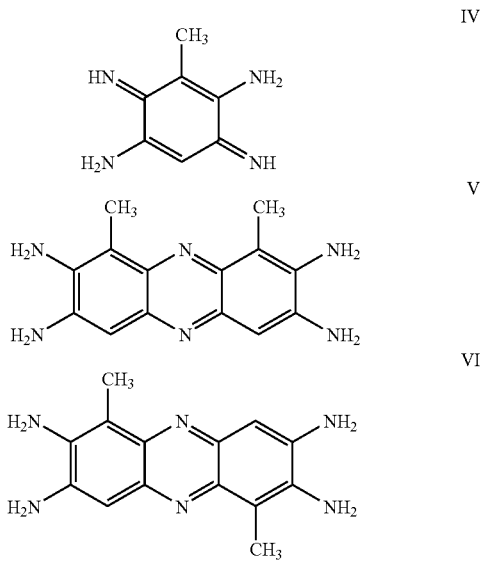

Unless otherwise defined, all technical and scientific terms used herein have the same meaning as commonly understood by one of ordinary skill in the art to which this invention belongs. In case of conflict, the present specification, including definitions, will control.

Although methods and materials similar or equivalent to those described herein can be used in the practice or testing of the present invention, suitable methods and materials are described herein.

Unless stated otherwise, all percentages, parts, ratios, etc., are by weight.

When an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

When the term "about" is used in describing a value or an end-point of a range, the disclosure should be understood to include the specific value or end-point referred to.

As used herein, the terms "comprises," "comprising," "includes," "including," "containing," "characterized by," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Use of "a" or "an" are employed to describe elements and components of the invention. This is done merely for convenience and to give a general sense of the invention. This description should be read to include one or at least one and the singular also includes the plural unless it is obvious that it is meant otherwise.

It is to be appreciated that certain features of the invention which are, for clarity, described above and below in the context of separate embodiments, may also be provided in combination in a single embodiment. Conversely, various features of the invention that are, for brevity, described in the context of a single embodiment, may also be provided separately or in any subcombination. Further, reference to values stated in ranges includes each and every value within that range.

What is claimed is:

1. An integrated process for preparing an isolated complex of 2,3,5,6-tetraminotoluene and the aromatic diacid XYTA, wherein the complex is generally described by Formula I

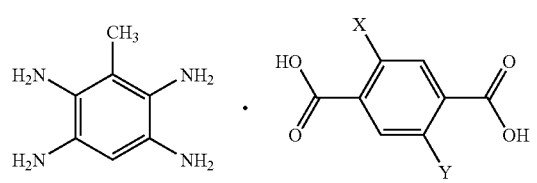

wherein X and Y are each independently selected from the group consisting of H, OH, SH, methyl, ethyl, F, Cl, and Br; comprising the sequential steps under exclusion of oxygen:
a) nitrating 2,6-dihalotoluene (II)

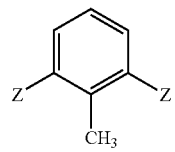

wherein each Z is independently Cl or Br, in a reaction mixture comprising oleum or $SO_3$, nitric acid, and $H_2SO_4$
wherein
(i) the concentration of nitric acid is about 2.0 to about 2.3 moles per mole of 2,6-dihalotoluene;
(ii) the concentration of $SO_3$ is about 1 to about 3 moles per mole of 2,6-dihalotoluene and (iii) the concentration of 2,6-dihalotoluene in the reaction mixture is between about 12 and about 24 weight percent; and
wherein the temperature of the reaction mixture does not exceed 120° C.; thereby producing 2,6-dihalo-3,5-dinitrotoluene;
b) directly separating the 2,6-dihalo-3,5-dinitrotoluene from the reaction mixture by filtration, while recycling the sulfuric acid mother liquor;
c) washing the 2,6-dihalo-3,5-dinitrotoluene with water or acid then water, then with $NH_4OH$, and then mixing it with glycol as a suspension;
d) aminating the 2,6-dihalo-3,5-dinitrotoluene by heating the suspension formed in step (c) to a temperature in the range of about 100° C. to about 160° C. and contacting it with $NH_3(g)$, thereby converting the 2,6-dihalo-3,5-dinitrotoluene to 2,6-diamino-3,5-dinitrotoluene;
e) directly separating the 2,6-diamino-3,5-dinitrotoluene from the reaction mixture by filtration, washing with glycol, then washing with water;
f) forming a slurry of the 2,6-diamino-3,5-dinitrotoluene with water and transferring the slurry to a hydrogenation reactor containing a hydrogenation catalyst to form a reaction mixture;
g) hydrogenating the 2,6-diamino-3,5-dinitrotoluene by contacting the reaction mixture formed in step (f) with hydrogen at a pressure in the range of about 0.31 to about 3.45 MPa and a temperature in the range of about 20° C. to about 100° C. to hydrogenate the 2,6-diamino-3,5-dinitrotoluene, thereby producing 2,3,5,6-tetraminotoluene;
h) contacting the 2,3,5,6-tetraminotoluene produced in (a) with an aqueous solution comprising 1 to 6 equivalents of acid per mol of 2,3,5,6-tetraminotoluene, optionally heating the solution, thereby dissolving the 2,3,5,6-tetraminotoluene;
i) filtering the reaction mixture, thereby removing the spent hydrogenation catalyst;
j) combining the filtered reaction mixture with
   i) 0 to 5 equivalents of an acid selected from the group consisting of HCl, acetic acid, $H_2SO_4$, and $H_3PO_4$;
   ii) 0 to 5 equivalents of an organic base or an inorganic base;
   iii) optionally, a buffer solution; and
   iv) an XYTA source selected from XYTA and $M_2$XYTA (Formula III)

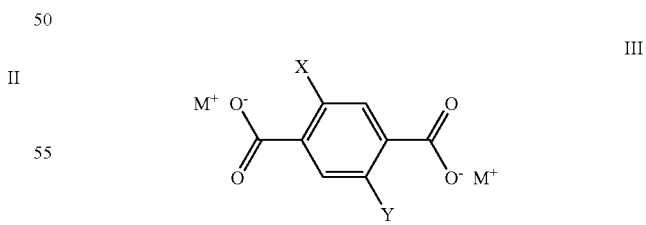

wherein M is K or Na, and wherein the molar ratio of XYTA to the 2,3,5,6-tetraminotoluene salt is from 1:1 to 1:1.1; thereby adjusting the pH of the mixture to between about 3 and about 10 and thereby producing and precipitating the complex generally described by Formula (I); and
k) cooling, filtering, and washing the isolated and precipitated complex.

2. The process of claim 1 wherein X=Y=OH, M=K, Z=Cl, the acid in steps (h) and (j) is HCl, and the pH is adjusted to about 5 to about 8 in step I.

3. The process of claim 1 wherein the glycol used in step (e) is distilled and recycled.

4. The process of claim 1 wherein the spent hydrogenation catalyst of step (i) is recovered and recycled.

5. The process of claim 1 wherein, in step (k), the precipitated complex is washed with water and methanol, and the methanol is recycled.

6. An integrated process for preparing an isolated complex of 2,3,5,6-tetraminotoluene and the aromatic diacid XYTA, wherein the complex is generally described by Formula I

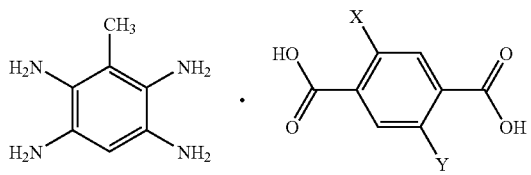

wherein X and Y are each independently selected from the group consisting of H, OH, SH, methyl, ethyl, F, Cl, and Br; comprising the sequential steps under exclusion of oxygen:
a) nitrating 2,6-dihalotoluene (II)

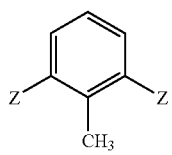

wherein each Z is independently Cl or Br, in a reaction mixture comprising oleum or $SO_3$, nitric acid, and $H_2SO_4$
wherein
(i) the concentration of nitric acid is about 2.0 to about 2.3 moles per mole of 2,6-dihalotoluene;
(ii) the concentration of $SO_3$ is about 1 to about 3 moles per mole of 2,6-dihalotoluene; and
(iii) the concentration of 2,6-dihalotoluene in the reaction mixture is between about 12 and about 24 weight percent; and
wherein the temperature of the reaction mixture does not exceed 120° C.; thereby producing 2,6-dihalo-3,5-dinitrotoluene;
b) directly separating the 2,6-dihalo-3,5-dinitrotoluene from the reaction mixture by filtration, while recycling the sulfuric acid mother liquor;
c) washing the 2,6-dihalo-3,5-dinitrotoluene with water or acid then water, then with $NH_4OH$, and then mixing it with glycol as a suspension;
d) aminating the 2,6-dihalo-3,5-dinitrotoluene by heating the suspension formed in step (c) to a temperature in the range of about 100° C. to about 160° C. and contacting it with $NH_3(g)$, thereby converting the 2,6-dihalo-3,5-dinitrotoluene to 2,6-diamino-3,5-dinitrotoluene;
e) directly separating the 2,6-diamino-3,5-dinitrotoluene from the reaction mixture by filtration, washing with glycol, then washing with water;
f) forming a slurry of the 2,6-diamino-3,5-dinitrotoluene with water and transferring the slurry to a hydrogenation reactor containing a hydrogenation catalyst to form a reaction mixture;
g) hydrogenating the 2,6-diamino-3,5-dinitrotoluene by contacting the reaction mixture formed in step (f) with hydrogen at a pressure in the range of about 0.31 to about 3.45 MPa and a temperature in the range of about 20° C. to about 100° C. to hydrogenate the 2,6-diamino-3,5-dinitrotoluene, thereby producing 2,3,5,6-tetraminotoluene;
h) contacting the 2,3,5,6-tetraminotoluene produced in (g) with an aqueous solution comprising 1 to 6 equivalents of acid per mol of 2,3,5,6-tetraminotoluene, optionally heating the solution, thereby dissolving the 2,3,5,6-tetraminotoluene;
i) filtering the reaction mixture, thereby removing the spent hydrogenation catalyst;
j) forming and precipitating the 2,3,5,6-tetraminotoluene salt by adding an acid to the filtered reaction mixture, wherein the acid is selected from the group consisting of HCl, acetic acid, $H_2SO_4$, and $H_3PO_4$;
k) cooling, filtering, washing and dissolving the precipitated 2,3,5,6-tetraminotoluene salt to form an aqueous solution thereof;
l) combining the 2,3,5,6-tetraminotoluene salt solution with
(i) 0 to 5 equivalents of an acid selected from the group consisting of HCl, acetic acid, $H_2SO_4$, and $H_3PO_4$;
(ii) 0 to 5 equivalents of an organic base or an inorganic base;
(iii) optionally, a buffer solution; and
(iv) 0 to 5 equivalents of an XYTA source selected from XYTA and $M_2XYTA$ (Formula III)
wherein M is K or Na, and wherein the molar ratio of XYTA to the 2,3,5,6-tetraminotoluene salt is from 1:1 to 1:1.1; thereby adjusting the pH of the mixture to between about 3 and about 10 and thereby producing and precipitating the complex generally described by Formula (I); and
m) cooling, filtering, and washing the isolated and precipitated complex.

7. The process of claim 6 wherein the acid in step (j) is HCl.

8. The process of claim 6 wherein the acid in step (j) is added in the gaseous state.

9. The process of claim 6 wherein the acid is added in step (j) an amount of about 6 to about 8 equivalents.

10. The process of claim 6 wherein X=Y=OH, M=K, Z=Cl, the acid in step (j) is HCl, and the pH is adjusted to about 5 to about 8 in step (I).

11. The process of claim 6 wherein the glycol used in step (e) is distilled and recycled.

12. The process of claim 6 wherein the spent hydrogenation catalyst of step (i) is recovered and recycled.

13. The process of claim 6 wherein, in step (m), the precipitated complex is washed with water and methanol, and the methanol is recycled.

* * * * *